(12) United States Patent
Morimoto

(10) Patent No.: US 9,351,802 B2
(45) Date of Patent: May 31, 2016

(54) ULTRASONIC SCALER TIP

(75) Inventor: Takashi Morimoto, Hyogo (JP)

(73) Assignee: YUGEN KAISHA SIESTA, Hyogo (JP)

( * ) Notice: Subject to any disclaimer, the term of this patent is extended or adjusted under 35 U.S.C. 154(b) by 0 days.

(21) Appl. No.: 13/503,912

(22) PCT Filed: Dec. 8, 2010

(86) PCT No.: PCT/JP2010/007154
§ 371 (c)(1),
(2), (4) Date: May 30, 2012

(87) PCT Pub. No.: WO2011/070782
PCT Pub. Date: Jun. 16, 2011

(65) Prior Publication Data
US 2012/0237895 A1    Sep. 20, 2012

(30) Foreign Application Priority Data
Dec. 10, 2009 (JP) .................. 2009-281046

(51) Int. Cl.
*A61C 3/03*    (2006.01)

(52) U.S. Cl.
CPC ........................ *A61C 3/03* (2013.01)

(58) Field of Classification Search
CPC .......... A61C 3/025; A61C 3/03; A61C 17/16; A61C 17/20; A61C 17/036
USPC ........................... 433/119, 165–166, 142–143
See application file for complete search history.

(56) References Cited

U.S. PATENT DOCUMENTS

| | | | | |
|---|---|---|---|---|
| 1,109,924 | A | * | 9/1914 | Hoffman et al. ............... 433/144 |
| 1,220,933 | A | * | 3/1917 | Bates ............................. 433/143 |
| 1,605,320 | A | * | 11/1926 | Bates ............................. 433/143 |
| 1,605,322 | A | * | 11/1926 | Bates ............................. 433/144 |
| RE29,687 | E | | 7/1978 | Sertich |
| 4,283,174 | A | * | 8/1981 | Sertich .......................... 433/119 |
| 4,283,175 | A | * | 8/1981 | Nash .............................. 433/119 |
| 4,613,307 | A | * | 9/1986 | Neumeyer ..................... 433/166 |
| 5,004,419 | A | * | 4/1991 | Kline ............................. 433/143 |
| 5,188,531 | A | * | 2/1993 | Von Sutfin .................... 433/118 |
| 5,388,989 | A | * | 2/1995 | Kountis ......................... 433/143 |
| 5,624,259 | A | * | 4/1997 | Heath et al. ..................... 433/72 |

(Continued)

FOREIGN PATENT DOCUMENTS

| | | |
|---|---|---|
| JP | 58-149695 | 4/1985 |
| JP | 60-58118 | 4/1985 |

(Continued)

OTHER PUBLICATIONS

International Search Report and Written Opinion for PCT/JP2010/007154 dated Jan. 25, 2011.

(Continued)

*Primary Examiner* — Cris L Rodriguez
*Assistant Examiner* — Hao D Mai
(74) *Attorney, Agent, or Firm* — Snell & Wilmer L.L.P.

(57) ABSTRACT

An ultrasonic scaler tip, capable of effectively removing tartar or the like adhered around an artificial tooth root, is provided. An ultrasonic scaler is also provided, which prevents metal material (for example, ion), except for titanium or titanium alloy, from adhering around the artificial tooth root and disturbing tissue growth and adhesion to the tooth root.

10 Claims, 10 Drawing Sheets

(56) References Cited

U.S. PATENT DOCUMENTS

| | | | |
|---|---|---|---|
| 5,704,787 A * | 1/1998 | Hickok et al. | 433/166 |
| 5,899,693 A * | 5/1999 | Himeno et al. | 433/119 |
| 6,257,887 B1 * | 7/2001 | Heckerman et al. | 433/141 |
| 6,893,260 B2 * | 5/2005 | Barnes et al. | 433/72 |
| 6,910,889 B1 * | 6/2005 | Hickok | 433/119 |
| 7,077,653 B2 * | 7/2006 | Haab | 433/143 |
| 2004/0023187 A1 * | 2/2004 | Hickok | 433/119 |
| 2004/0241608 A1 * | 12/2004 | Hickok | 433/119 |
| 2007/0224575 A1 * | 9/2007 | Dieras et al. | 433/119 |
| 2008/0248444 A1 * | 10/2008 | Bahcall et al. | 433/119 |
| 2009/0181342 A1 * | 7/2009 | Chien | A61C 1/07 433/119 |

FOREIGN PATENT DOCUMENTS

| | | |
|---|---|---|
| JP | 60-39889 | 9/1986 |
| JP | 61-156913 | 9/1986 |
| JP | 2-34737 | 3/1990 |
| JP | 07-330867 | 9/1996 |
| WO | WO 2009009909 A1 * | 1/2009 ............... A61C 8/00 |

OTHER PUBLICATIONS

An Office Action dated Apr. 24, 2014 in JP Application No. 201080055920.3.

Supplementary Search Report for EP 10835705.4 dated May 27, 2014.

Office Acton for Chinese Application Ser. No. 201080055920.3 dated Oct. 14, 2014.

Office Action dated Mar. 10, 2015 in Chinese Application No. 201080055920.3.

* cited by examiner

FIG. 6
(a)
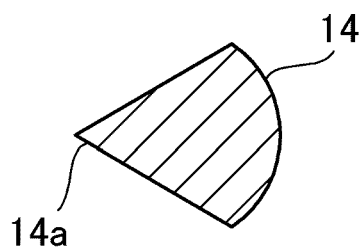
(b)
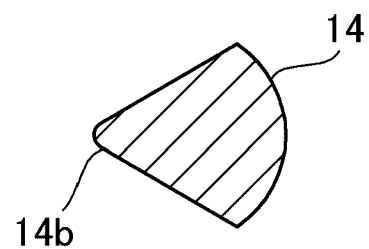

ULTRASONIC SCALER TIP

CROSS-REFERENCE TO RELATED APPLICATIONS

This application is a U.S. national phase filing under 35 U.S.C. §371 of PCT/JP/2010/007154 filed Dec. 8, 2010, which claims priority to and the benefit of Japanese Application No. 2009-281046 filed on Dec. 10, 2009. Both of the aforementioned applications are incorporated herein by reference in their entirety.

TECHNICAL FIELD

The present invention relates to a dental ultrasonic scaler tip.

BACKGROUND ART

Tartar and plaque are primary cause of periodontal diseases and dental caries. Therefore, it is important to remove tartar and plaque adhered to tooth surfaces, tooth root surfaces, restorative and prosthetic materials, or artificial tooth root materials in order to treat or prevent diseases related to the tooth. In such dental treatment, removal of tartar from tooth surfaces, debridement within pockets, and detoxification of tooth root surfaces to smoothen and polish the root surfaces, that is, scaling and root planing, are fundamental treatment of importance.

Scaling operation and root planing operation are normally performed using a metal scaler for hands, and in particular, a hand curette scaler. Scaling and root planing using such a hand curette scaler are however an operation that requires experience and skill and takes time and effort.

In addition to the method using a hand curette scaler, scaling and root planing can be performed using therapeutic instruments, such as Rotosonic for engines, an air scaler for turbines, or an ultrasonic scaler. Among the therapeutic instruments, the ultrasonic scaler is configured by connecting an ultrasonic oscillation source for oscillating ultrasonic waves of a predetermined oscillation frequency with a dental tip of a predetermined shape.

The dental tip is made as an integrated instrument from a base end portion to a tip portion thereof. The base end portion of the dental tip is connected to the ultrasonic oscillation source. When the ultrasonic oscillation source is oscillated in the ultrasonic wave band, the ultrasonic oscillation is transferred from the base end portion of the tip to the tip portion of the tip. Thereafter, pressing the tip portion against a treatment area on the tooth surface will grind and remove tartar or the like.

Conventionally, Japanese Laid-Open Publication No. 8-229054 (Reference 1), Japanese Laid-Open Publication No. 10-28694 (Reference 2) and Japanese Laid-Open Publication No. 5-154164 (Reference 3) disclose tips of various shapes.

As illustrated in FIGS. 11 and 12, the following method is publicly known: a pin-shaped artificial tooth root 12, referred to as an implant, is implanted into a bone 20 at an upper jaw or a lower jaw; An abutment 16 is screwed to be attached to a threaded hole formed in an end portion of the artificial tooth root 12 protruded from the bone 20; and subsequently, an artificial crown 18 is put on the abutment 16 from above.

When tartar or the like adhered around the artificial tooth root is tried to be removed using the conventional tip, the removal is not efficiently performed because the conventional tip described above is mainly for removing tartar and plaque that are adhered around a natural tooth.

CITATION LIST

Patent Literature
PLT 1
  Japanese Laid-Open Publication No. 8-229054
PLT 2
  Japanese Laid-Open Publication No. 10-28694
PLT 3
  Japanese Laid-Open Publication No. 5-154164

SUMMARY OF INVENTION

Technical Problem

The present invention is intended to solve the conventional technique described above. An objective of the present invention is to provide an ultrasonic scaler tip capable of efficiently removing tartar or the like adhered around an artificial tooth root.

Another objective of the present invention is to provide an ultrasonic scaler tip, which prevents metal material (for example, ion), except for titanium or titanium alloy, from adhering around the artificial tooth root and disturbing tissue growth and adhesion to the tooth root.

Solution to Problem

Accordingly, the present invention provides the following.

A scaler tip according to the present invention is attached to a tip portion of a dental ultrasonic scaler with an oscillator provided therein, the scaler tip comprising: a tip body made of titanium or titanium alloy, wherein a tip portion of the tip body is formed with a curved portion, which can make a contact in a curved shape along a periphery of an artificial tooth root.

Preferably, in the scaler tip according to the present invention, a base end portion of the tip body is detachably attached to the tip portion of the dental ultrasonic scaler.

Still preferably, in the scaler tip according to the present invention, the curved portion includes an interior surface that lies along an outer circumference of the artificial tooth root.

Still preferably, in the scaler tip according to the present invention, the curved portion includes an interior surface with a diameter corresponding to an outer diameter of the artificial tooth root.

Still preferably, in the scaler tip according to the present invention: a shape of a section of the curved portion is a substantial triangle or a substantial trapezoid, an acute angle portion with a pointed tip is formed on a side surface of the curved portion, and the acute angle portion can be inserted into a thread groove of the artificial tooth root.

Still preferably, in the scaler tip according to the present invention, the curved portion includes a circular arc interior surface that lies along an outer circumference of the artificial tooth root, and the curved portion is formed to fit into a thread groove formed on an outer circumference of the artificial tooth root.

Still preferably, in the scaler tip according to the present invention, a radius of curvature of the curved portion is 1.0 mm to 8.0 mm, and an outer diameter of a section of the curved portion is 0.3 mm to 0.8 mm.

Advantageous Effects of Invention

According to the scaler tip of the present invention, the curved portion is formed at the tip portion of the tip body, which tip portion can make contact in a curved shape along the periphery of an artificial tooth. Thereby, the curved portion makes contact to the periphery of the artificial tooth root while oscillating, and the curved portion fits, in particular, into a thread groove formed around the artificial tooth root, so that it becomes possible to efficiently remove tartar or the like adhered around the artificial tooth root.

Further, the tip is made of titanium or titanium alloy. Therefore, in a case where the tip makes a contact to the periphery of the artificial tooth root by ultrasonic oscillation, even if the titanium or titanium alloy is adhered to the periphery of the tooth root, it does not disturb tissue growth and adhesion to the artificial tooth root.

In particular, when the tip is made of titanium alloy, the shape of the tip can be readily processed to fit the periphery of the artificial tooth root.

BRIEF DESCRIPTION OF DRAWINGS

FIG. 4(a) illustrates the curved portion with a surface thereof shaped in a substantial semicircle. FIG. 4(b) illustrates the curved portion with a surface thereof shaped in a circular arc.

FIG. 6 is a cross sectional view illustrating various embodiments of an ultrasonic scaler tip according to the present invention.

DESCRIPTION OF EMBODIMENTS

Figure 1:
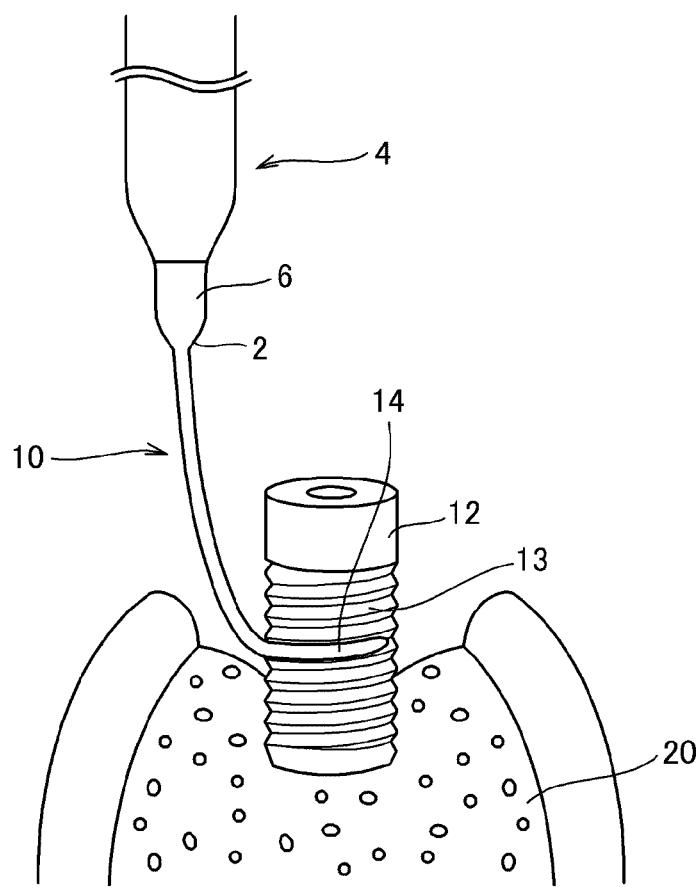
FIG. 1 is a schematic view illustrating use of an ultrasonic scaler tip according to the present invention attached to a dental ultrasonic scaler.

Hereinafter, an embodiment of the present invention will be described.

As illustrated in FIGS. 1 to 4, a dental scaler tip 2 according to the present invention is attached to a dental ultrasonic scaler 4, which looks sort of like a hand piece. A motor and an oscillator (not shown) are respectively provided inside the dental ultrasonic scaler 4, and oscillation is transferred to a tip portion of the scaler tip 2.

The scaler tip 2 includes a tip body 10 made of titanium or titanium alloy. The tip body 10 is formed as one piece comprised of a base end portion 6 with a relatively larger outer diameter, and a tip portion 8. The scaler tip 2, as a whole, has a shape that is tapered from the base end portion 6 to the tip portion 8. The scaler tip 2 includes a curved portion 14 formed at the tip portion 8 of the tip body 10. The curved portion 14 can make a contact along the periphery of an artificial tooth root 12, and is in a shape of a curved rod.

Figure 2:
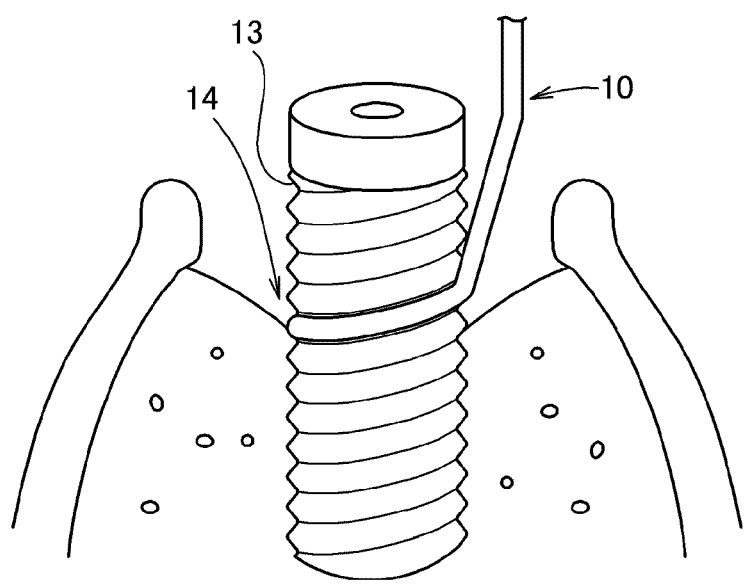
FIG. 2 is an enlarged view of an essential part of an ultrasonic scaler tip according to the present invention.
Figure 3:
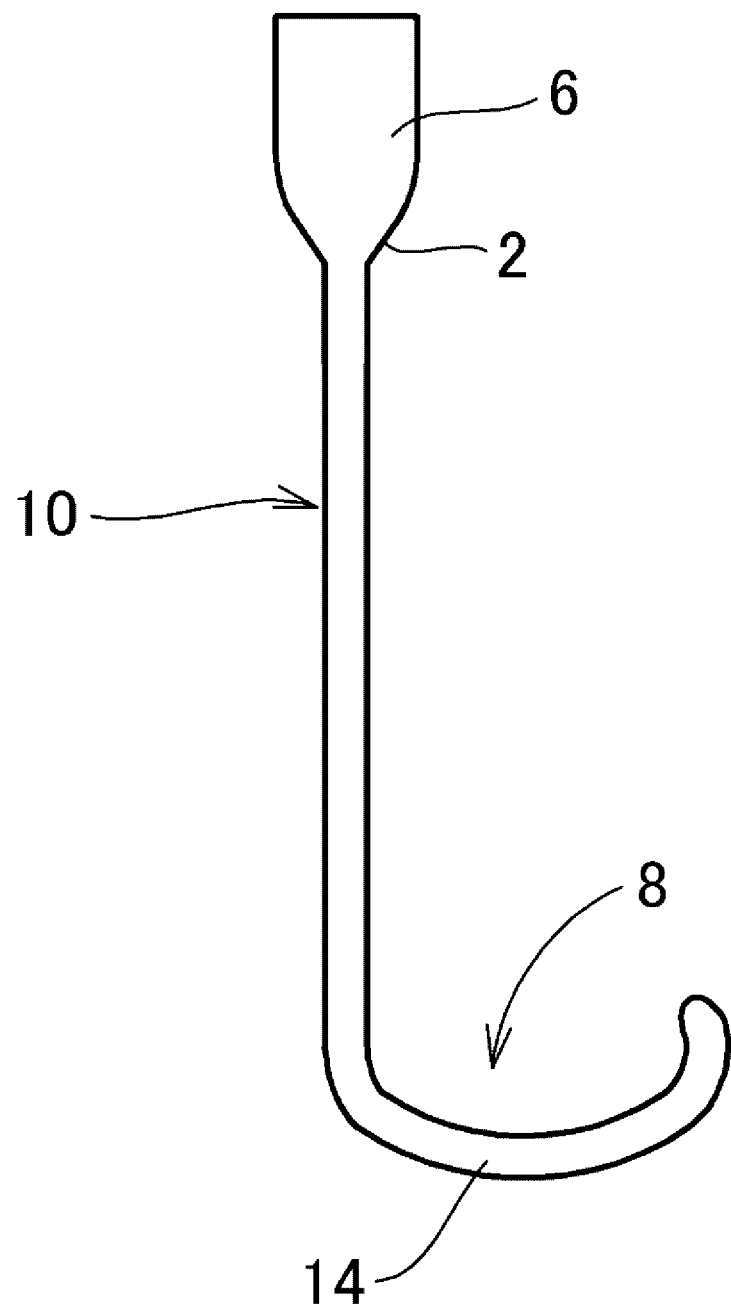
FIG. 3 is a schematic elevation view of an ultrasonic scaler tip according to the present invention.
Figure 4:
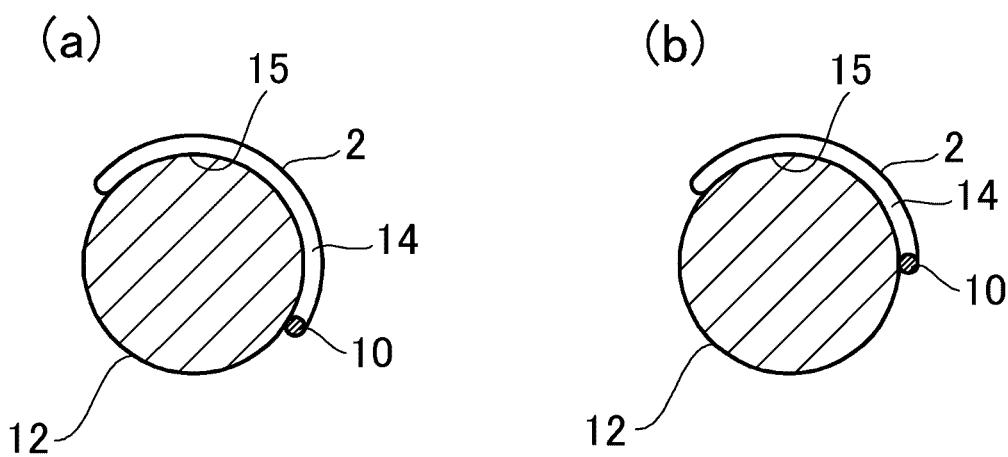
FIG. 4 is a cross sectional view of an ultrasonic scaler tip according to the present invention, a curved portion of which lies along an outer circumference of an artificial tooth root.

As illustrated in FIG. 4(a), the curved portion 14 may be formed to include an interior surface 15 of a substantial semicircle, with a diameter corresponding to the outer diameter of the artificial tooth root 12. Alternatively, as illustrated in FIG. 4(b), the curved portion 14 may be formed to include an interior surface 15 of a circular arc that lies along an outer circumference surface of the artificial tooth root 12. That is, the inner diameter of the curved portion 14 and the shape of the interior surface 15 thereof are formed in such a manner to lie along a thread groove 13 formed in the outer circumference of the artificial tooth root 12 as well as to allow the curved portion 14 to fit into the thread groove 13 (FIGS. 1 and 2).

For example, the inner diameter of the curved portion 14 illustrated in FIGS. 4(a) and 4(b) is preferably 1.0 mm to 8.0 mm. The inner diameter of the curved portion 14 is still preferably 2.0 mm to 6.0 mm. The radius of curvature of the curved portion 14 is preferably 1.0 mm to 8.0 mm. The radius of curvature of the curved portion 14 is still preferably 0.5 mm to 4.0 mm, and most preferably, 1.0 mm to 3.0 mm.

The outer diameter of a section of the curved portion 14 is set to allow the curved portion 14 to fit into the thread groove 13 of the artificial tooth root 12. The outer diameter is normally 0.3 mm to 0.8 mm (and preferably 0.5 mm to 0.8 mm). The pitch of the thread groove 13 of the artificial tooth root 12 is about 0.6 mm as the narrowest, and therefore, the thread groove 13 is configured to allow the curved portion 14 to fit.

The shape of a section of the curved portion 14 can be a substantial triangle or a substantial trapezoid, as illustrated in FIGS. 6(a) and 6(b). Tip portions 14a and 14b are formed on a side portion of the curved portion 14. It is preferable that the tip portions 14a and 14b have an acute angle so that the tip portions 14a and 14b can easily fit into the thread groove 13. As illustrated in FIGS. 1 and 2, the tip body 10 may be crooked or curved.

The scaler tip 2 may be formed by bend-processing a member made of titanium or titanium alloy. The scaler tip 2 may also be molded using a metal mold.

As illustrated in FIGS. 1 and 2, the tip 2 is normally manufactured by curve-processing the tip portion 8 of the tip body 10, which is made of metal. The base end portion 6 of the tip body 10 is formed with a diameter that is larger than the tip portion 8, and the base end portion 6 is detachably attached to an end portion of the dental ultrasonic scaler 4. Normally, a female threaded hole (or a male screw) or the like is formed at the base end portion 6 of the tip body 10, and a male screw (or a female threaded hole) formed at the tip portion of the scaler 4 is screwed into the hole (or the screw).

The shape of the tip is changeable. It is also possible to prepare various sizes of tips in accordance with the size of the artificial tooth root 12.

Figure 5:
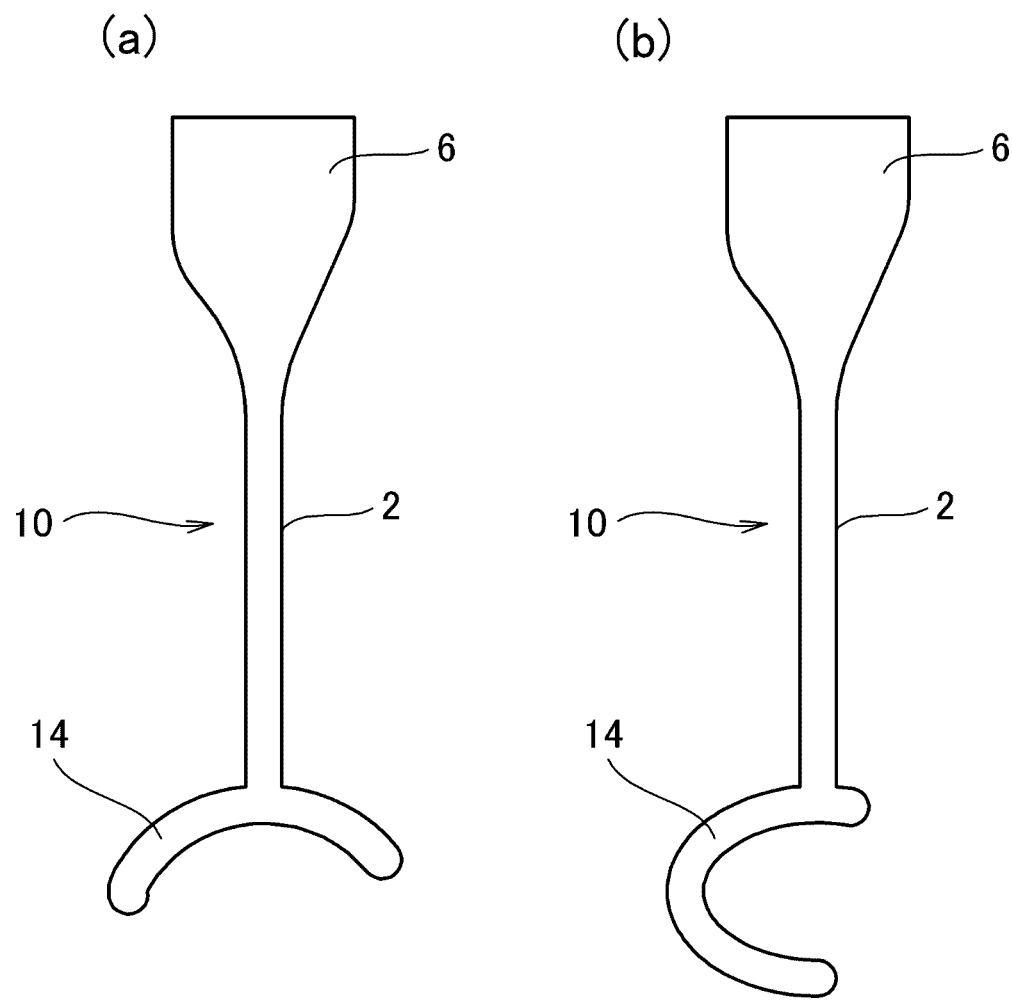
FIG. 5 is a schematic view illustrating various embodiments of an ultrasonic scaler tip according to the present invention.

For example, as illustrated in FIG. 5(*a*), the tip 2 may be formed by extending the tip body 10 from a substantially center portion of the curved portion 14. As illustrated in FIG. 5(*b*), the tip 2 may be formed by extending the tip body 10 from the vicinity of the end portion on one side of the curved portion 14.

In use of the scaler tip 2 of the present invention, as illustrated in FIG. 1, the tip 2 is attached to the tip portion of the scaler 4. The tip 2 is inserted such that the curved portion 14 lies along the outer circumference of the artificial tooth root 12. When an operation switch of the scaler 4 is turned on, an ultrasonic oscillator provided inside the scaler 4 starts oscillating. By the driving, the curved portion 14 of the tip 2 oscillates, so that tartar or the like around the artificial tooth root 12 can be removed. Since the shape of the tip portion 8 of the tip body 10 is curved, the cleaning around the artificial tooth root 12 can be performed with a wide area and efficiently.

In addition, since the tip is made of titanium or titanium alloy, iron component will not adhere to the periphery of the artificial tooth root, and tissue growth and adhesion to the artificial tooth root will not be disturbed unlike a conventional stainless tip.

An appropriate size of the tip 2 is selected in accordance with the outer diameter, shape or the like of the artificial tooth root 12. Further, by preparing a plurality of types of tips with different sizes and shapes, and selecting one of them in accordance with the size or the like of a patient's artificial tooth root, an effective removal can be made in accordance with the condition of the artificial tooth root.

FIGS. 7 to 10 each illustrate various tips.

Figure 7:
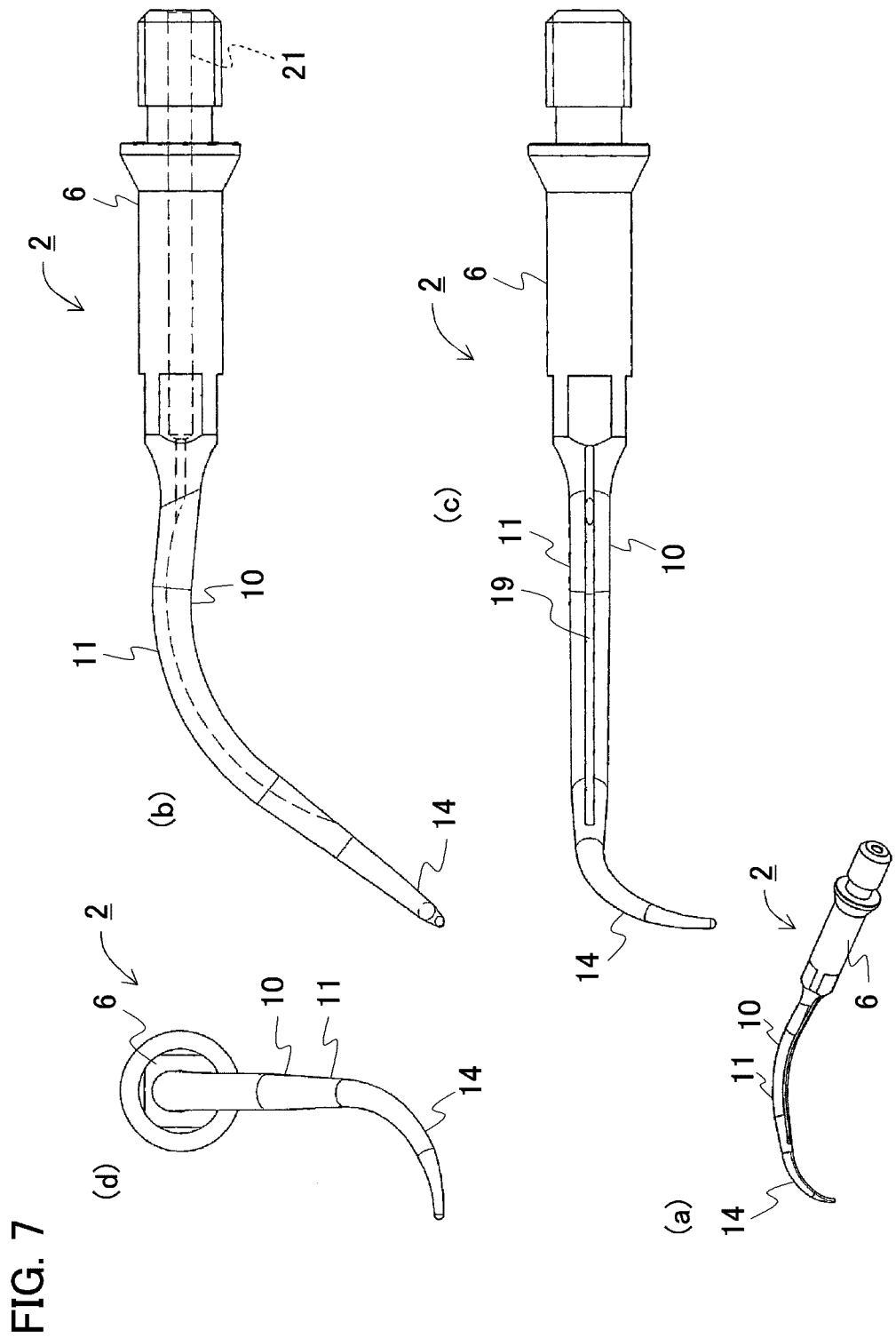
FIG. 7(a) is a perspective view of one embodiment of an ultrasonic scaler tip according to the present invention.
FIG. 7(b) is a front elevation view thereof.
FIG. 7(c) is a plan view thereof.
FIG. 7(d) is a side view thereof.
Figure 8:
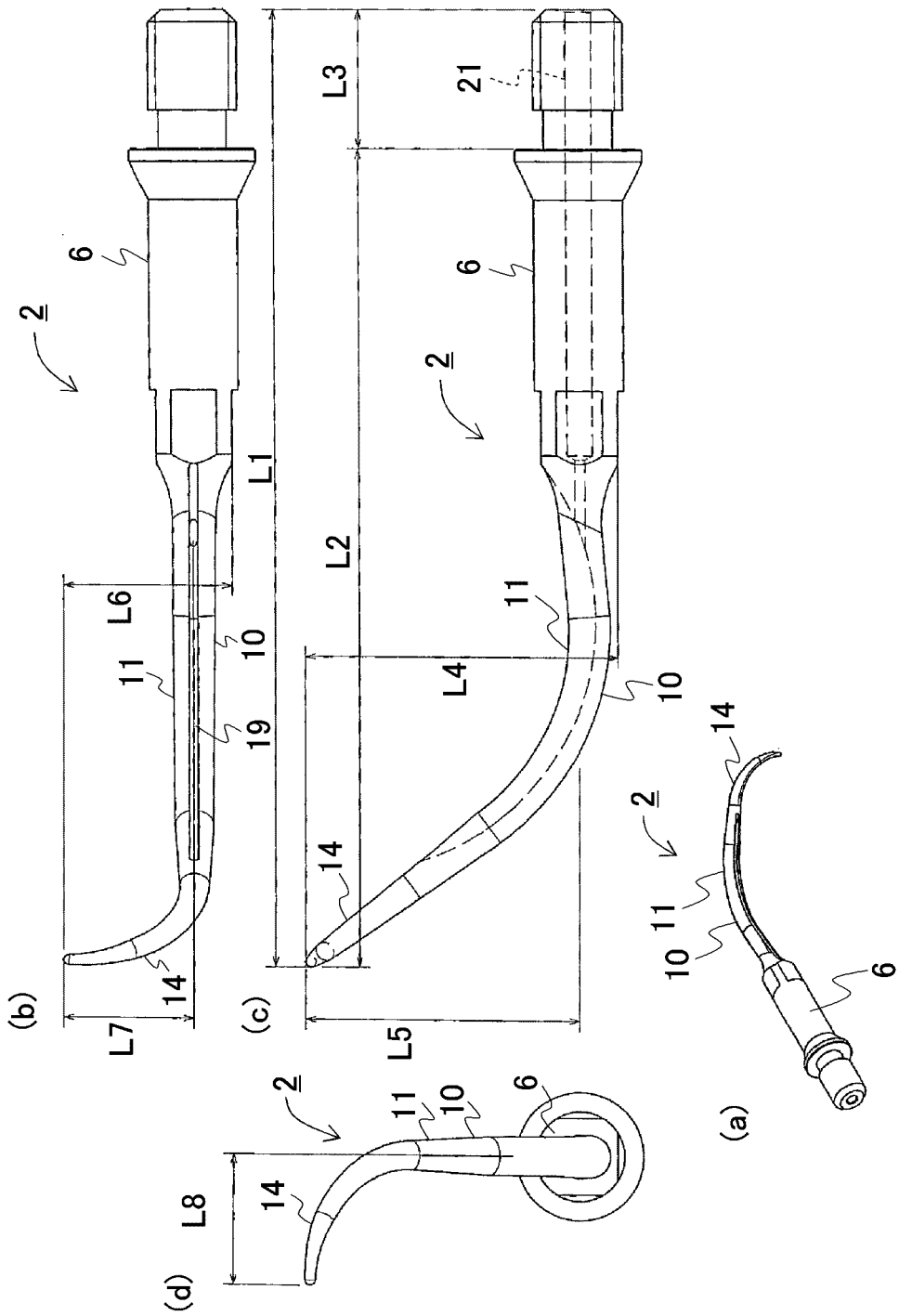
FIG. 8(a) is a perspective view of another embodiment of an ultrasonic scaler tip according to the present invention.
FIG. 8(b) is a front elevation view thereof.
FIG. 8(c) is a plan view thereof.
FIG. 8(d) is a side view thereof.

The tips illustrated in FIGS. 7 and 8 are in an relationship of enantiomorphic symmetry. The tips illustrated in FIGS. 7 and 8 include a tip body 10 made of titanium or titanium alloy, and the base end portion 6 of the tip body 10 has an outer diameter of 2.5 mm to 3.5 mm (preferably 2.8 mm to 3.2 mm) and a length of 5 mm to 12 mm. A middle portion 11 of the body is curved 7 mm to 12 mm (preferably 9 mm to 10 mm) to the side from the based end portion 6. The tip portion 8 of the body 10 is further curved 3 mm to 5 mm (preferably 3.5 mm to 4.5 mm) from the tip of the middle portion 11, in a direction crossing substantially 80 degrees to 100 degrees with the curving direction of the middle portion 11. The radius of curvature of the curved portion 14 is 2.0 mm to 6.0 mm (preferably 3.0 mm to 5.0 mm). A path 21, for passing cold water therethrough, is formed inside the body 10, and a groove 19 is formed on a side portion of the body 10.

In FIG. 8, a preferable range of each of L1 to L8 is as follows:
L1: 33 mm to 40 mm (preferably 36 mm to 39 mm);
L2: 28 mm to 36 mm (preferably 30 mm to 34 mm);
L3: 4 mm to 8 mm (preferably 5 mm to 6 mm);
L4: 10 mm to 14 mm (preferably 11 mm to 13 mm);
L5: 8 mm to 14 mm (preferably 10 mm to 12 mm);
L6: 5 mm to 9 mm (preferably 6 mm to 8 mm);
L7: 3 mm to 6 mm (preferably 4 mm to 5 mm); and
L8: 2 mm to 6 mm (preferably 3 mm to 5 mm).

Figure 9:
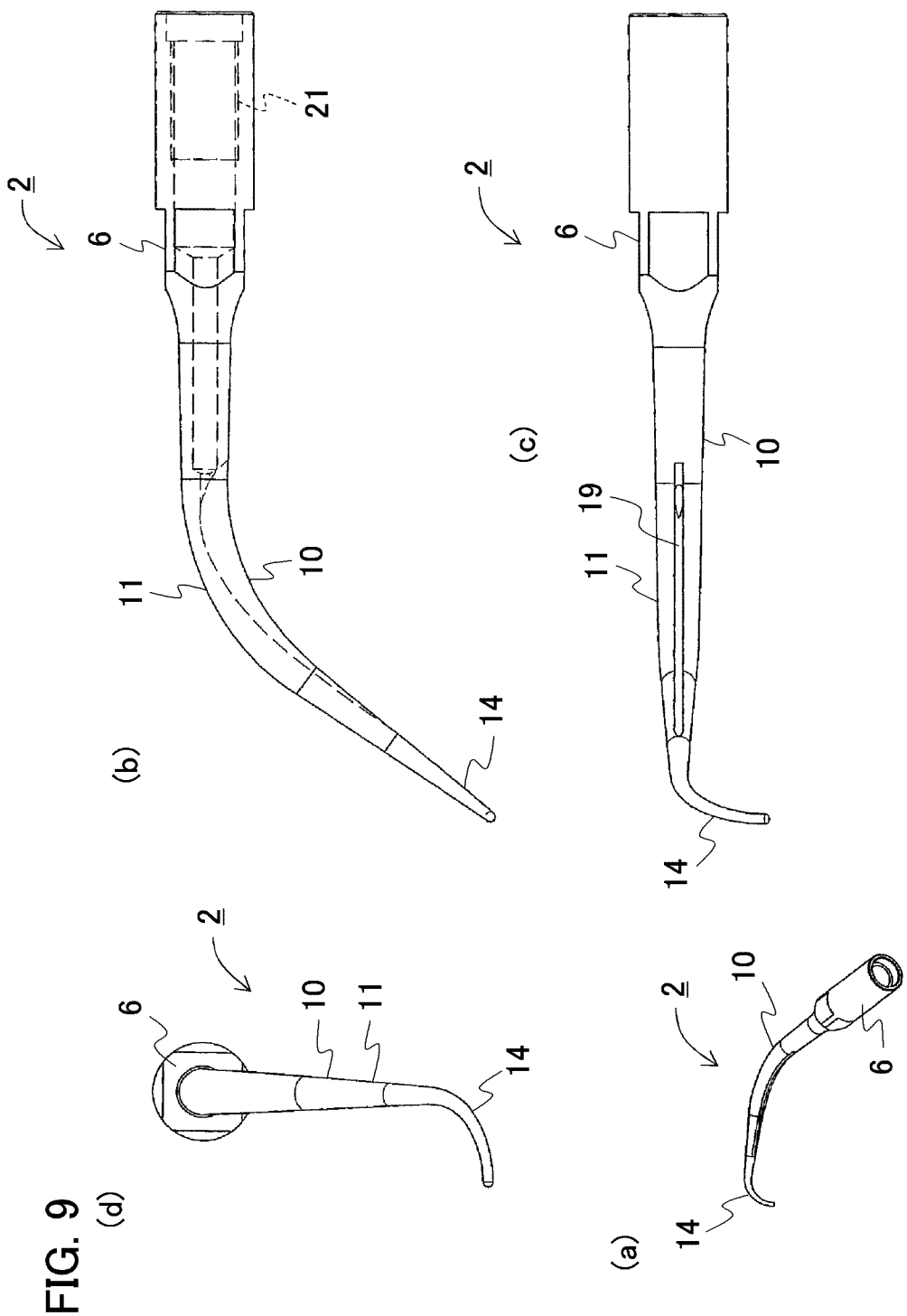
FIG. 9(a) is a perspective view of still another embodiment of an ultrasonic scaler tip according to the present invention.
FIG. 9(b) is a front elevation view thereof.
FIG. 9(c) is a plan view thereof.
FIG. 9(d) is a side view thereof.
Figure 10:
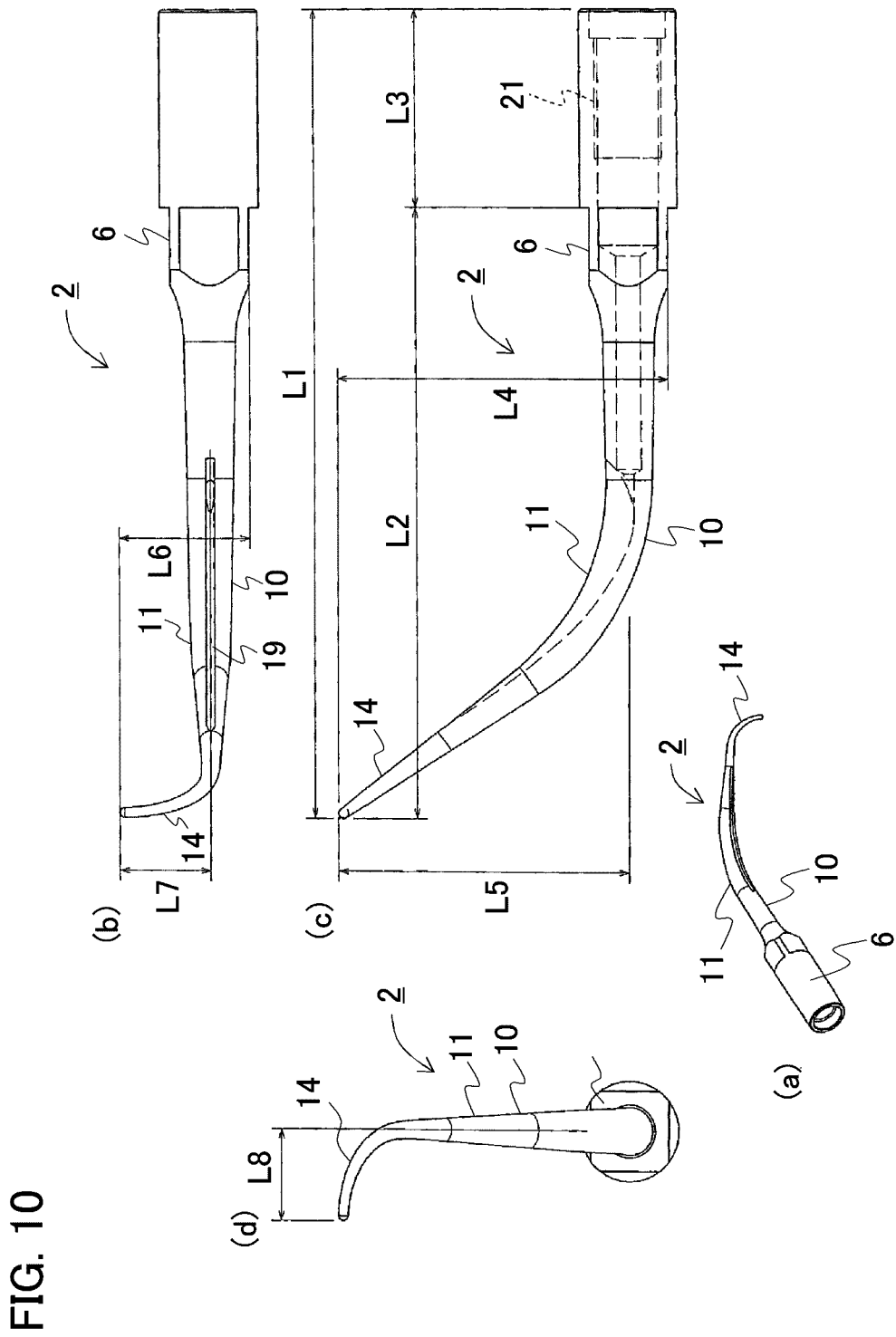
FIG. 10(a) is a perspective view of still another embodiment of an ultrasonic scaler tip according to the present invention.
FIG. 10(b) is a front elevation view thereof.
FIG. 10(c) is a plan view thereof.
FIG. 10(d) is a side view thereof.
Figure 11:
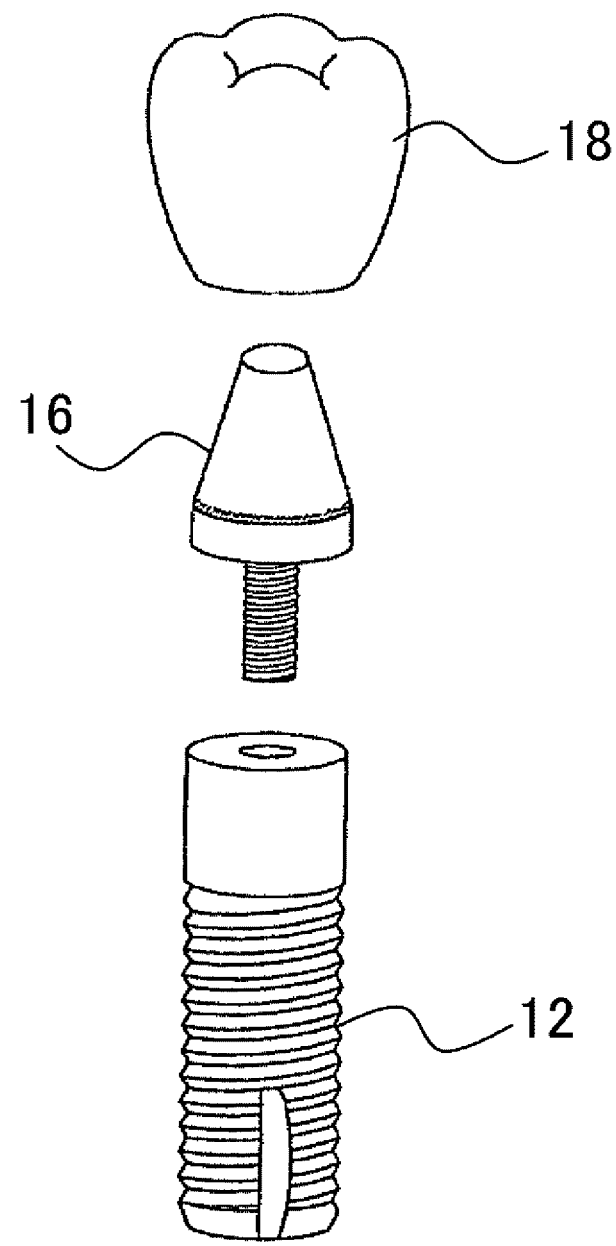
FIG. 11 is an exploded perspective view of a conventional artificial tooth root with an abutment attached thereon and a dental prosthesis crown being put from above.
Figure 12:
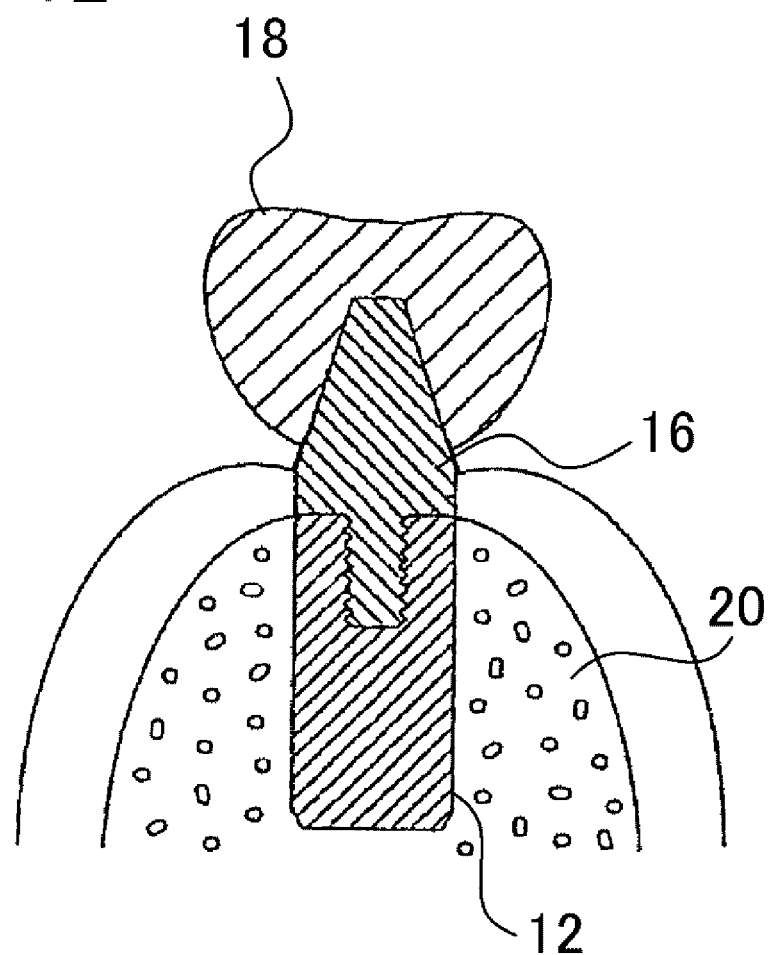
FIG. 12 is a cross sectional view of a conventional artificial tooth root fixed to the alveolar bone, with an abutment attached to a tip of the artificial tooth root, and a dental prosthesis crown being put from above.

The tips illustrated in FIGS. 9 and 10 are in a relationship of enantiomorphic symmetry. The tips illustrated in FIGS. 9 and 10 include a tip body 10 made of titanium or titanium alloy, and the base end portion 6 of the tip body 10 has an outer diameter of 2.5 mm to 3.5 mm (preferably 2.8 mm to 3.2 mm) and a length of 5 mm to 12 mm. A middle portion 11 of the body is curved 7 mm to 12 mm (preferably 9 mm to 10 mm) to the side from the based end portion 6. The tip portion 8 of the body 10 is further curved 3 mm to 5 mm (preferably 3.5 mm to 4.5 mm) from the tip of the middle portion 11, in a direction crossing substantially 80 degrees to 100 degrees with the curving direction of the middle portion 11. The radius of curvature of the curved portion 14 is 2.0 mm to 6.0 mm (preferably 3.0 mm to 5.0 mm). A path 21, for passing cold water therethrough, is formed inside the body 10, and a groove 19 is formed on a side portion of the body 10.

In FIG. 10, a preferable range of each of L1 to L8 is as follows:
L1: 28 mm to 36 mm (preferably 31 mm to 34 mm);
L2: 22 mm to 28 mm (preferably 23 mm to 26 mm);
L3: 6 mm to 10 mm (preferably 7 mm to 9 mm);
L4: 11 mm to 15 mm (preferably 12 mm to 14 mm);
L5: 10 mm to 14 mm (preferably 11 mm to 13 mm);
L6: 3 mm to 7 mm (preferably 4 mm to 6 mm);
L7: 2 mm to 5 mm (preferably 3 mm to 4 mm); and
L8: 2 mm to 5 mm (preferably 3 mm to 4 mm).

The outer diameter of the curved portion 14 becomes smaller towards the tip portion, in the tip of any embodiment. The outer diameter of the base portion of the curved portion 14 is preferably 0.5 mm to 0.8 mm, and the outer diameter of the tip of the curved portion 14 is preferably 0.2 mm to 0.5 mm.

INDUSTRIAL APPLICABILITY

By removing tartar and plaque adhered to the artificial tooth root, it becomes possible to treat or prevent diseases related to the tooth.

REFERENCE SIGNS LIST

2 ultrasonic scaler tip
4 scaler
6 base end portion
8 tip portion
10 tip body
14 curve portion

The invention claimed is:

1. A dental assembly comprising:
an artificial tooth root, wherein the artificial tooth root has a thread groove formed on an outer circumference of the artificial tooth root,
a dental ultrasonic scaler with an oscillator provided therein, the dental ultrasonic scaler comprises:
a first scaler tip and a second scaler tip, the first scaler tip and the second scaler tip are detachably attached to a tip portion of the dental ultrasonic scaler,
wherein the first scaler tip and the second scaler tip each comprises:
a tip body made of titanium or titanium alloy, wherein a tip portion of the tip body comprises a curved portion, wherein the tip body is in a first plane, the curved portion is in a second plane, and the first plane is normal to the second plane, wherein an end of the curved portion interfaces with the tip body,
wherein when the artificial tooth root is implanted and embedded within a jaw bone with a gap existing between the jawbone and the artificial tooth root, the curved portion is configured to be inserted through the gap and pushed into the thread groove while turning the tip body, such that the curved portion is configured to make contact in a spiral shape along a periphery of the thread groove of the artificial tooth root, wherein the curved portion is configured to contact the thread groove over an entire length of the curved portion, wherein the curved portion includes an interior surface that is configured to lie along the outer circumference of the artificial tooth root, wherein the interior surface of the curved portion has a diameter corresponding to an outer diameter of the artificial tooth root, and wherein the first scaler tip and the second scaler tip are in a relationship of enantiomorphic symmetry.

2. The dental assembly according to claim 1, wherein:
a shape of a cross-section of the curved portion is a substantial triangle or a substantial trapezoid;
wherein an acute angle portion with a pointed tip is formed on a side surface of the cross-section;
and the acute angle portion is configured to be inserted into the thread groove of the artificial tooth root.

3. The dental assembly according to claim 1, wherein a radius of curvature of the curved portion is 1.0 mm to 8.0 mm, and an outer diameter of a section of the curved portion is 0.3 mm to 0.8 mm.

4. The dental assembly according to claim 1, wherein the interior surface of the curved portion is of a substantial semi-circle.

5. The dental assembly according to claim 1, wherein the tip body is formed as one piece including a base end portion and the tip portion.

6. The dental assembly according to claim 1, wherein the tip body includes a base end portion, a middle portion and the curved portion, and
wherein the middle portion of the tip body is curved to a side from the based end portion, and the curved portion of the tip body is curved from a tip of the middle portion, in a direction crossing substantially 80 degrees to 100 degrees with a curving direction of the middle portion.

7. The dental assembly according to claim 1, wherein the curved portion of the first scaler tip and the curved portion of the second scaler tip are in a relationship of enantiomorphic symmetry.

8. A method of removing tartar adhered around an artificial tooth root that is implanted and embedded within a jaw bone with a gap exists between the jaw bone and the artificial tooth root, wherein the artificial tooth root has a thread groove formed on an outer circumference of the artificial tooth root, the method comprising:
providing a dental ultrasonic scaler with an oscillator provided therein, the dental ultrasonic scaler comprises: a first scaler tip and a second scaler tip detachably attached to a tip portion of the dental ultrasonic scaler; wherein the first scaler tip and the second scaler tip each comprises:
a tip body made of titanium or titanium alloy, a tip portion of the tip body comprises a curved portion, wherein the tip body is in a first plane, the curved portion is in a second plane, and the first plane is normal to the second plane; an end of the curved portion interfaces with the tip body, wherein the curved portion is configured to make contact in a spiral shape along a periphery of the thread groove of the artificial tooth root, wherein the curved portion is configured to contact the thread groove over an entire length of the curved portion, the curved portion includes an interior surface that is configured to lie along an outer circumference of the artificial tooth root, wherein the interior surface with a diameter corresponding to an outer diameter of the artificial tooth root, and wherein the first scaler tip and the second scaler tip are in a relationship of enantiomorphic symmetry;
selecting one of the first scaler tip and the second scaler tip, while the dental ultrasonic scaler is oscillating and oscillation is transferred to the curved portion of said selected one of the first scaler tip and the second scaler tip, inserting said curved portion of said selected one of the first scaler tip and the second scaler tip through the gap and into the thread groove of the artificial tooth root, such that the inserted curved portion makes contact in a spiral shape along a periphery of the thread groove of the artificial tooth root, the inserted curved portion contacts the thread groove over an entire length of the inserted curved portion, and the interior surface of the inserted curved portion lies along the outer circumference of the artificial tooth root;
turning the tip body of the said selected one of the first scaler tip and the second scaler tip to remove the tartar adhered around the artificial tooth root.

9. The method according to claim 8, wherein:
a shape of a cross-section of the curved portion is a substantial triangle or a substantial trapezoid; wherein an acute angle portion with a pointed tip is formed on a side surface of the cross-section; and the acute angle portion is configured to be inserted into a thread groove of the artificial tooth root.

10. The method according to claim 8, wherein a radius of curvature of the curved portion is 1.0 mm to 8.0 mm, and an outer diameter of a section of the curved portion is 0.3 mm to 0.8 mm.

* * * * *